United States Patent
Slesarev et al.

(10) Patent No.: US 7,112,564 B2
(45) Date of Patent: Sep. 26, 2006

(54) BIODEGRADABLE GLUCOSAMINEMURAMYL PEPTIDES FOR APOPTOSIS MODULATION

(75) Inventors: Vladimir Ivanovich Slesarev, Boyds, MD (US); Todor Vassilev Dimitrov, Chestnut Hill, MA (US)

(73) Assignee: Zylacta Corporation, Boyds, MD (US)

( * ) Notice: Subject to any disclaimer, the term of this patent is extended or adjusted under 35 U.S.C. 154(b) by 67 days.

(21) Appl. No.: 10/409,846

(22) Filed: Apr. 9, 2003

(65) Prior Publication Data

US 2004/0203090 A1 Oct. 14, 2004

(51) Int. Cl.
*A61K 38/16* (2006.01)

(52) U.S. Cl. .......................................... 514/8
(58) Field of Classification Search ................. 514/8
See application file for complete search history.

(56) References Cited

U.S. PATENT DOCUMENTS

| | | | |
|---|---|---|---|
| 4,395,399 A * | 7/1983 | Ovchinnikov et al. ... | 424/279.1 |
| 4,545,932 A | 10/1985 | Takase | |
| 5,834,435 A | 11/1998 | Slesarev | |
| 6,506,388 B1 | 1/2003 | Shionoya | |
| 2001/0034325 A1* | 10/2001 | Slesarev ........................ | 514/8 |

OTHER PUBLICATIONS

Ghuysen, Use of Bacteriolytic Enzymes in Determination of Wall Structure and Their Role in Cell Metabolism, Bacteriological Reviews, Dec. 1968, pp. 425-464.*
See http://www.chemqmul.ac.uk/iumb/enzyme/EC3/4/24/75.html, printed May 31, 2005, p. 1.*
Guinand, et al., Enzymatic Obtention of Biologically Active Glycopeptides from Actinomadura R 39, Biological Properties of Peptidoglycan, Second, Proceeding of the International Workshop, 1986, Meeting Date 1985, pp. 389-394.*
DNA Isolation Protocols Biomolecule Teaching Guide, Patrick, Supplement IVA, Mar. 4, 2003, pp. 1 and 1-8, http://www.rpc.msoe.edu/sepa/preview//sec4/4-a-6.htm, printed May 31, 2005.*
Fountoulakis, et al. Effect of Strong Detergents and Chaotropes on the Detection of Proteins in Two-Dimensional Gels, Electrophoresis, 2001, 22, 1593-1602.*
Sharmar, Anker SD. Cytokines, apoptosis(abstract) cachexia: the potential for TNF. antagonism. Int. J. Cardiology, 2002; 85:161-71.
Argiles JM. Int. J. Biochem Cell Biol Abstract 2003, 35: 405-409.
Castellanos M. Stroke, 2002 Abstract v33:982-987.
Cusack MR. Amer. Coll Cardiology Abstract 2002, 39: 1917-1923.
Agnoletti L. Circulation, 1999 v. 100: 1983-1991.
Affords Molecular Pathology (Abstract) 2002, v. 53 : 55-63.
Kurzrock R Cancer, 2001 v92 : 1684-1688 (Abstract).
McGuire SO Experimental Neurology, 2001, V169, 219-30 (Abstract).
Barone F.C. Stroke, 1997, v. 28: 1233-1244.
Armstrong L. Thorax, 1997, V.52 : 442-446.
Ridker P., Circulation, 2000, v. 101 p. 2149-2153.
Jaeckhke H., J. Immunogy, 1998 v. 160 : 3480-3486.
Smarmavk Expert Opin Investig (Abstract) Drugs, 2003, 12: 139-152.
Stammch, Circulation, v. 101 suppl l. 350-351.
Zanotti S., Expert Opin Investig Drugs,2002 v. 11: 1061-75 (Abstract).
Niermaus A., Intensive Care Med. 2003 v.21 (Abstract).
Yan R, Zhonghua Zhen Xing Shao Shang Nai 1997, B 368-72 (Abstract).
Jarrar D., AmJ. Physiol Lung Cell Mol Physiol 2002, 283: 799-805 (Abstract).
Serteser M., J. Surg Res, 2002, 107: 234-40 (Abstract).
Oxman T., Amj. Physiol Heart Cre Physiol,278 M 1717-24.

* cited by examiner

*Primary Examiner*—Bruce R. Campell
*Assistant Examiner*—Jennifer Harle
(74) *Attorney, Agent, or Firm*—Hogan & Hartson L.L.P.

(57) ABSTRACT

The endopeptidase hydrolysis of cross link peptide bond of the peptidoglycans results in release of the novel glucosaminemuramyl tri, tetra, penta, hexa, and octapeptides. Their structure is defined by specific endopeptidase cleavage as well as genus of gram positive bacteria. They are potent cytoprotective agents capable of inhibiting of TNF alpha cytotoxicity.

16 Claims, 2 Drawing Sheets

Fig.1 Inhibition of LDH release by GMHP
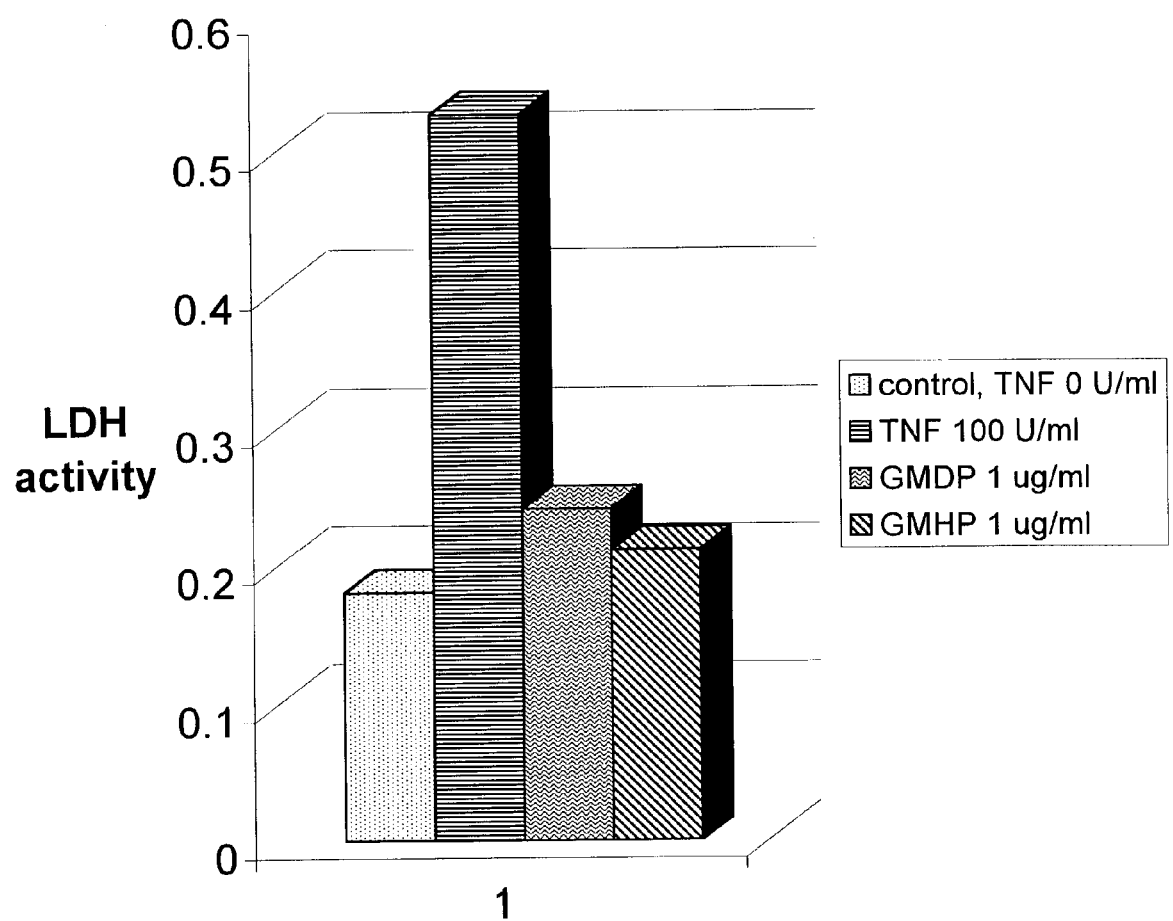

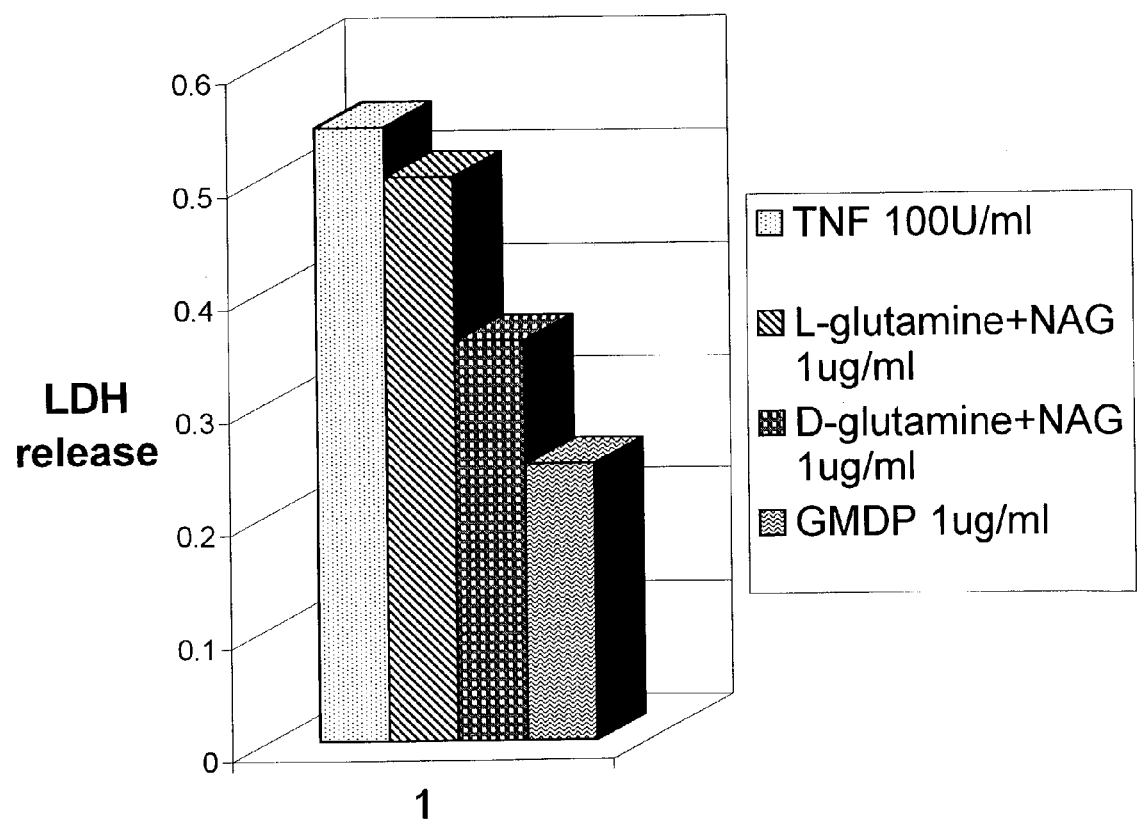
Fig2. D-aminoacids effects on LDH activity

BIODEGRADABLE GLUCOSAMINEMURAMYL PEPTIDES FOR APOPTOSIS MODULATION

FIELD OF THE INVENTION

The present invention relates to apoptosis modulating glucosamine-muramyl-peptides, obtained by specific endopeptidase digestion of gram positive bacteria, methods of preparation of thereof and medical food compositions for management and treatment of conditions caused by TNF alpha cytotoxicity.

BACKGROUND OF THE INVENTION

Apoptosis, or programmed cell death, is a naturally occurring process that plays a strong role in ensuring the development and maintenance of multicellular organisms by eliminating unwanted cells. However, if this process goes over stimulated, cell loss and degenerative disorders such as rheumatoid arthritis, chronic heart, liver and renal failure, adult respiratory distress syndrome, cachexia caused by cancer, stroke, heart attack and heart failure can result. (Sharma R., and Anker S D, Int. J. Cardiol., 2002, 85:161–171, Argiles J M et al., Int. J. Biochem Cell Biol., 2003, 35:405–409, Castellanos M, et al., Stroke, 33:982–987, Cusack M R, et al., Amer. Coll. Cardiol., 2002, 39:1917–23, Agnoletti L. et al, Circulation, 1999, 100: 1983–1991).

Mediators, which can trigger apoptosis include TNF alpha, Fas and transforming growth factor beta, neurotransmitters, growth factor withdrawal, loss of extracellular matrix attachment and extreme fluctuations in intracellular calcium levels (Afford and Randhawa, Mol. Pathol., 2000, 53:55–63). Among them TNF alpha killing pathways are considered as a most common route of apoptosis signaling. This cytokine is also involved in cancer related fatigue, leucopenia, anemia, and thrombocytopenia (Kurzrock R., Cancer, 2001, 92: 1684–8,). TNF alpha is also implicated in the development of the neurodegenerative disorders such as Alzheimer's and Parkinson's disease, ALS, rhinitis pigmentosa and multiple sclerosis (McGuire S O et al., Exp Neurol., 2001, 169:219–230). Its pathogenetic role is crucial in the development of the extensive brain, lung, and heart damage (Barone F. C. et al, Stroke, 1997, 28:1233–1244, Armstrong L. et al., Thorax, 1997, 52:442–446,). Plasma concentrations of TNF alpha are persistently elevated among patients after myocardial infarction (Ridker P., et al, Circulation, 2000, 101:2149–2153)

With the identification of the systemic TNF alpha response as a major component in the pathogenesis of the septic shock syndrome (Jaecshke H., et al J. Immunol., 1998, 160:3480–3486), much of the recent work has focused on modulating of this response. High-flow haemofiltration was offered to clean both endotoxin and cytokines (Sharma V K and Dellinger R P, Expert Opin Investig Drugs, 2003, 12:139–152). Hypotensive and proinflammotory effects of TNF alpha were inhibited by soluble receptors/receptor antagonists and anti-inflammatory cytokines such as interleukine10. The current experimental therapies involve transforming growth factor-beta, granulocyte colony-stimulating factor, interferon phi and anti TNF alpha antibody (Stamm Ch., et al, Circulation, 101, suppl. 1, 350–351). Moreover, less known cytokines such as macrophage migration inhibitory factor and high mobility group I protein will be clinically tested (Zanotti S., et al., Expert Opin Investig Drugs, 2002, 11:1061–75).

Another preliminary study has demonstrated that recombinant GM-CSF upregulates HLA-DR expression on monocytes, thus reversing the immunoparalysis in patients with severe sepsis. Moreover, there was a concurrent increase of whole blood TNF response. (Nierhaus A., et al. Intensive Care Med, 2003, 21).

The same situation was noticed in rats with burn shock. Nonsurvival group had lower levels of serum G-CSF and higher content of TNF alpha compared with survival. Supplement of GM-CSF could significantly improve animal survival with burn wound infection following severe burn shock (Yan R., et al. Zhonghua Zhen Xing Shao Shang Wai Ke Za Zi, 1997, 13:368–372). Serum TNF alpha was also elevated after soft tissue trauma and hemorrhagic shock, which leads to the acute respiratory distress syndrome (ARDS) {Jarrar D, et al. Am. J. Physiol. Lung Cell Mol. Physiol., 2002, 283:799–805}.

Ischemia/reperfusion (I/R) induces a cytokines response and production of reactive oxygen species, which affects the organs remote to the sites of I/R. Yet, hepatic TNF alpha was implicated in playing major role in the liver damage during renal surgery (Serteser M., et. Al., J. Surg Res, 2002, 107:234–40).

Intravenous injection of whole lactobacillus reduced tachyarrhythmia significantly and improved recovery of the ischemized rat heart (Oxman T., et al, Am J Physiol Heart Circ Physiol, 278, H1717–H1724).

However, a broad variety of biodegradable glucosaminemuramyl peptides were not isolated and tested for cytoprotective effects.

BRIEF SUMMARY OF INVENTION

The present invention is based on the discovery that hydrolysis of the peptide bonds and peptide cross link of the gram positive bacteria leads to release of the novel glucosamine muramyl peptides, with strong potency towards inhibition of TNF alpha cytotoxicity. Consequently, in one aspect the invention provides new biodegradable glucosaminemuramyl tri, tetra-, penta-, hexa-, and octapeptides, which possess apoptosis modulating properties and are useful for treating all conditions with elevated serum lactate dehydrogenase activity. Examples of such conditions are ischemic reperfusion injury, atherosclerosis, heart attack, cerebral infarction, and chronic heart failure. Applicants also demonstrated that enhanced cytoprotective properties of these muramyl peptides are caused by the presence of two and more D-amino acids covalently bound L-amino acids.

Another aspect of the present invention is to provide a method for isolation of high purity biodegradable glucosaminemuramyl peptides, which comprises the bacterial wall isolation with subsequent lysozyme and endopeptidase hydrolysis and purification with preparative high pressure liquid chromatography (HPLC).

Yet, another aspect of this invention is a preparation of the medical food for dietary management of all conditions caused by elevation of TNF alpha and LDH.

Novel medical food consisting of the hydrolyzed bacterial wall or whole bacteria can be used for reduction of the systemic cytokine toxicity, which leads to elevation of LDH and cachexia. Such medical food may be used to reduce LDH associated malignancy and damage caused by radiation therapy and chemotherapy. Specifically, the present food may be recommended for those patients who suffer from common postchemotherapy toxicity such as leukocytopenia, thrombocytopenia, and high bilirubin with elevated liver enzymes. Further, the present invention provides nutrition for reducing cancer fatigue and muscle dystrophy.

In a related aspect, the present invention provides a food useful for treating patients suffering from hepatotoxicity caused by chemicals, anesthetics, drugs, and alcohol. Glucopeptide fortified food and drink may be especially beneficial for people with concurrent liver cirrhosis, thus preventing severe fatigue and brain damage caused by ammonia. Furthermore, presented invention provides the food for metabolic detoxifications of the cancerogenic chemicals and mutagens.

Still another aspect of the present invention includes dietary methods of inhibiting dermal apoptosis, thereby reducing clinical symptoms of psoriasis.

While another aspect of this invention is to provide a method of lung protection in the patients with pulmonary diseases such as adult respiratory distress syndrome, fibrosis, and cardiogenic lung edema.

BRIEF DESCRIPTION OF THE DRAWINGS

For further details, reference is made to the discussion which follows, in light of the accompanying drawings, wherein:

FIG. 1 illustrates the cytoprotective potency of the novel GMHP in comparison with GMDP.

FIG. 2 demonstrates inhibition of TNF alpha cytotoxicity by D-amino acids in combination with the same concentration of N-acetyl-glucosamine.

DETAILED DISCRIPTION OF THE INVENTION

The present invention relates to the novel glucosaminemuramyl three-, tetra-, and pentapeptides, obtained by specific endopeptidase digestion, medical food and drinks, containing, as effective component, glucopeptide extracted from Gram positive bacteria. This invention also provides medical food for specific inhibition of TNF alpha cytotoxicity, which may be administered orally to humans in single dose as small as 1 mg/kg. The dosage of 2–10 mg/kg may be preferable.

For the safety reasons, glucopeptide complexes from lactic acid bacteria such as Lactobacillus or Bifidum may be preferable.

Glucosaminemuramyl tetrapeptide is a basic unit of the glucoproteins-peptidoglycans. In the cell wall they are bound to teicholic acid and polysaccharides by a phosphate diester band. Peptidoglycan strands are cross-linked to each other to form a large sheet that surrounds the cell. Cross links are formed between two tetrapeptides on adjacent glycan strands. The $\epsilon NH_2$ group of diaminopimelic acid in the third position on 1 glycan bonds with COOH group of D-alanine on an adjacent glycan in *Lactobacillus Plantarum*. Majority bacteria of the species of *lactobacillus* have L-lysine or L-ornithine instead of diaminopimelic acid. The peptide bond forms a cross-link between adjacent glycan strands. It is important to point out that 60–90% of the total basic units are bound to the adjacent glycan strands in the gram positive bacteria. Obviously, there is a need to hydrolyze this cross link in order to release novel biologically active glucosaminemuramyl peptides. Recently, bromelain and lysine endopeptidases have been offered for digestion of *Brevibacterium flavum*, *Corynebacterium herculis*, and *Corynobacterium glutamicum* (Shionoya et al, 2003, U.S. Pat. No. 6,506,388). However, neither bromalain, nor lysine-endopeptidase can cleave the direct cross link between diaminopimelic acid and D-alanine in the peptidoglycan chain of these bacteria. As a result, the suggested enzymes are useless for preparation of glucosamine muramyl tri-tetra-, and pentapeptides from these bacteria. Recently, only glucosaminemuramyl-L-alanine,D-glutamyl-diaminopimelic acid (tripeptide) and, tetrapeptide from *L. Plantarum* have been isolated (Takase et al, U.S. Pat. No. 4,545,932, 1985).

Tripeptide (glucosaminemuramyl-L-alanine, D-glutamyl-diaminopimelic acid) was prepared by applying diminopimelic acid-D-alanine peptidase. Immunostimulating properties of this tetrapeptide were well characterized.

However, absolute majority of yogurt bacteria of genus *lactobacillus* and *bifidum* have a different structure of their basic peptidoglycan unit. Glucosaminemuramyl tetrapeptide contains L-lysine, or L-ornithine in the third position instead of diaminopimelic acid. Moreover, the peptide subunits of the peptidoglycan are cross-linked weather by single D-isoasparaginyl residues, or complex residues of L- or D-amino acids, selected from the group of serine, alanine, threonine, glycine, and glutamine. Therefore, there is a real practical need to release from large peptidoglycan chain a significant amount of biologically active glucosamine di-, tri-, tetra-, penta-, and hexapeptides.

The presence of two, or three D-amino acids could enhance the cytoprotective properties described for glucosamine-muramyl-dipeptide.

For this purpose, inventors have proposed to hydrolyze cross link peptide bonds. Cleavage of this bond can also be done by hydrolysis of carboxyl bond of the aspartic acid or carboxyl bonds of L-lysine in the third position. A broad variety of specific endopeptidase which cleaves the carboxyl bond of glutamic acid, glycine, serine, threonine, lysine, aspartic acid, alanine-alanine can be used. They are of plant, bacterial, or animal origin.

In the present invention, the bacteria are necessarily specific bacteria, because they produce a different cross link residues, which require a specific endopeptidase to hydrolyze a cross bond. However, in view of the safety and the utilization of waste material, lactate producing bacteria are preferable one, for example. *Lactobacillus acidophilus, bulgaricus, fermentum* or *Bifidobacterium infantis*.

Culture of bacteria belonging to genera of *Lactobacillus, Bifidobacterium*, and *Streptococcus thermophilus* can be made by a known method in an appropriate medium. Centrifuged cells, freeze dried cells, heat killed cells, and spray-dried cells can be used for the purpose of production of novel glucosamine muramyl peptides.

They can be prepared whether by digestion of isolated bacterial wall preparations, or by digestion of the whole bacteria with following purification by gel filtration on sephadex. The washed bacterial cells should be treated with pronase or papain to dissolve the surface proteins then they are boiled for 10 min in ion detergent. 5% sodium dodecyl sulphate can be recommended as a detergent for separation of bacterial wall from protoplast. The protoplast is discarded as supernatant after centrifuging at 10000 rpm for 20 min. Elimination of the protoplast effectively purify the active decomposed material of the present invention as in the examples.

The peptide cross link bond of these bacterial wall a can be hydrolyze by trypsin and glycine-endopeptidase, which are also food additives. Temperature 27–30° C., pH 6,0 during 4–6 hours are considered the optimal conditions.

Glycan moiety can be decomposed by lysozyme. The lysozyme hydrolysis is considered optimal under temperature of 55° C., pH=6.0 during 48 hours.

The both enzymes can be eliminated by ultrafiltration with 3000 D cutoff. Highly concentrated solution of the novel glucosaminemuramyl peptides can be obtained after reverse osmosis. Novel biodegradable glucosaminemuramyl peptide can be identified by analytical reverse phase HPLC with following isolation and purification by preparative HPLC.

The centrifuged cells for whole bacteria digestion are purified by pronase or papain treatment.

Then biomass is diluted in the distilled water in the ratio 1:10 for lysozyme hydrolysis. The protoplast (as a pellet fraction) is discarded after centrifuging at 4000 rpm for 1 hour. The supernatant is concentrated by factor 4 after ultrafiltration with 3000 D cutoff and nanofiltration with reverse osmosis.

Routine methods for purifications of glycopeptides complexes can be employed. More specifically, hydrolysis obtained by aforementioned methods, is applied to anion-exchange column to remove lysozyme and high-molecular nuclear acids. Further, protease and nuclease can be used for degradation of the remaining proteins and nuclear acids, respectively. Hydrophobic chromatography may be used to remove enzymes by passing them through a column with resin. Glucosaminemuramyl peptide composition may be fractioned by gel chromatography A broad variety of specific endopeptidases can be applied to hydrolyze a cross interpeptide bond. For the safety reason trypsin (E.C.3.4.21.4) and glycine-endopeptidase (E.C.3.4.22.25) are preferable one.

For example, glycine-endopeptidase or peptidase B was isolated from *Papaya Carica*. Unlike papain, it cleaves the bond on carboxyl terminal of glycine, a residue, which crosses links the basic peptidoglycan units of *Bifidobacterium Infantis, B.Breve, B.Asteroides, B.Parvulorum, B.Globosum*, and *Streptococus Viridance*.

Such specifically targeted cleavage of cross link bond results in the releasing of the novel biodegradable peptides: N-acetyl-glucosamine-N-acetyl-muramyl-L-Ala-D-isoGlu-L-Lys-D-Ala, and

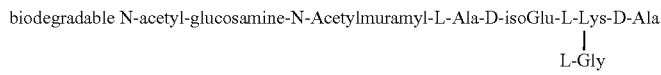

Trypsin and lysyl endopeptidase ((E.C.3.4.24.50) cleave the bond on the carboxyl end of lysine. Such specific cleavage leads to release to a novel tripeptide N-Acetyl-N-glucosamine-N-Acetyl-muramyl-L-Ala-isoGlu-L-Lys and

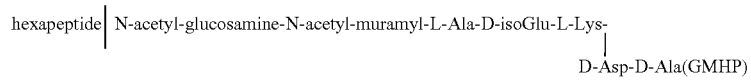

after proteolysis of the petidoglycan of *Lactobacillus Bulgaricus, L. helveticus, L. jugurti L. lactis, L. Acidophilus, L. salivarius, L. delbruckii, L. leichmannii, L. jensenii, L. casei, L. rhamnosus, L. tolerans, L. fusiformis, L. pseudoplantarum, L. coryneformis, L. torquens, L. curvatis, L. xylosus, L. zeae, L. brevis, L. buchneri, L. fructovoranse, L. malefermentans, L. pastorianus, L. parvus, L. frigidus, L. hilgardii, Bifudobacterium eriksonii, B. coryneforme*, and *B. indicum*.

Short term digestion of peptidoglycan of the same bacteria with flavastacin (E.C.3.4.24.76) cleaves peptide bond on N terminal of aspartic acid. It causes a release of another novel biodegradable pentapeptide:

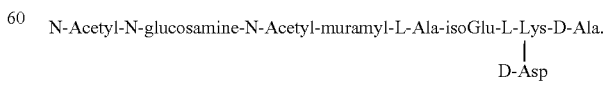

The flavostatin digestion of the *B. Bifidum* results in the release of another novel hexapeptide

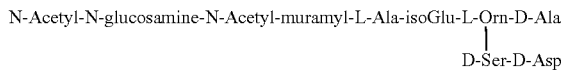

*F. flavastacin* hydrolysis of peptidoglycan of *L. fermentum* leads to release of novel

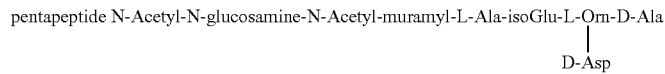

Yet, another endopeptidase saccharalysine (E.C.3.4.24.37) can be used for cleavage of cross peptide Ala—Ala link. Saccharalysine hydrolysis of *Lactobacillus coprophilus, Bifidobacterium globosum, Streptoccocus thermophilus, Leuconostoc paramesenteroides*, and *amelibiosus* leads to release the novel

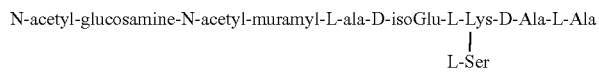

The saccharilysine hydrolysis of cross peptide link in the peptidoglycan chain of *Lactobacillus minor, Bifidobacterium adolescentis, Leuconostoc lactis, L. lactophilum, L. cremoris* and *L. mesenteroides* leads to the novel

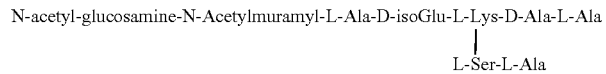

The cross link cleavage of peptidoglycan of *Bifidobacterium lactentis, B. longum, B. suis* by the same endopeptidase can lead to another novel. Method of claim 1 where the biodegradable compound is

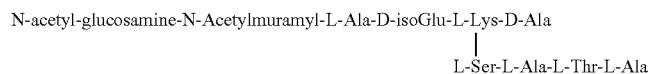

Yet another aspect of this invention is to prepare biodegradable GMDP, which is commercially available as semi synthetic or synthetic drug. Enzymatic hydrolysis of every gram positive or negative bacteria can be accomplished with peptydyl-lysine metallopeptidase or V8 endopeptidase (E.C.3.4.21.82) derived from *S. aureous*. Peptydyl-lysine metallopeptidase (E.C.3.4.24.20) cleaves the N terminal of lysine. V8 endopeptidase hydrolysis carboxyl bond of glutamic acid, thus releases natural GMDP.

The antiapoptotic properties for the semi synthetic analog GMDP were demonstrated previously (Slesarev V., 1998, U.S. Pat. No. 5,834,435). However, biodegradable glucosamine tri-, tetra-, penta-, hexa-, and octapeptide never been isolated and tested for the inhibition of TNF alpha cytotoxicity. It also worthy to point out, they have more than one D-amino acid, which are capable of enhancing cytoprotective properties.

The inventors have demonstrated that the presence of at least two D-amino acids increases cytoprotective potency in comparison with GMDP.

Daily peptidoglycan dosage in the range of from 50 mg to 2000 mg may be found to be acceptable for dietary management of TNF alpha cytotoxicity with optimal range of 200–1500 mg per day. Daily isolated disaccharide tetra-, penta-, and hexapeptide dosage in the range offrom 10 mg to 100 mg would acceptable with optimal range 10–50 mg.

When the glucosaminemuramyl peptides of the present invention are applied as a main medical agent, it can orally be used in powder, tablets, dispersion, capsules, confectionery, drinks or the like.

When they are used as a pharmaceutical or cosmetic agent, it can be administered orally, rectally, or vaginally in sprays, tablets, suppositories, or capsules.

DESCRIPTION OF THE PREFERRED EMBODIMENTS

Specific production embodiments are presented hereinafter.

EXAMPLE 1

Isolation of N-acetyl-glucosamine-N-acetyl-muramyl-L-Ala-D-isoGlu-L-Lys-D-Asp-D-Ala from *Lactobacillus bulgaricus*

1. Biomass Preparation

Fermentation of *Lactobacillus bulgaricus* was done in 300 L fermenter with working volume of 220 L. Liquid nutrient medium was composed of 10 g/L of yeast extract, 20 g/L glucose, 20 g/L pepton+beef extract, 2 g/L $K_2HPO_4$, 5 g/L $CH_3COONa$, 0.2 g/L $MgSO_4$, 0.05 g/L $MnSO4$, and 0.1 g/L Tween 80.

Fermenting was made anaerobic conditions at temperature 40+−3° C. Fermenting period was 22 hours. Biomass was separated from the suspension on centrifuge Sorvall 3B at 4000 r/min. Moisture biomass yield was 1.6 kg, dried one −440 g. Wet biomass was rinsed twice by 1 L of distilled water, then was suspended in 1 L of CH3COONa for 2–4 hours, and again was rinsed by water using centrifuge Servile-5B at 8000 r/min. Biomass was exposed for 1–2 hours in 1 L of $CH_3COONa$ at 60–80° C. and rinsed by distilled water. Then, 50–70% ethanol was used to rinse the biomass until supernatant liquid becomes colorless. 96% ethanol was used to stabilize the biomass. This processing was needed to preserve the biomass at room temperature for following hydrolysis. Moisture biomass should be stored at −60° C.

2. Hydrolysis.

1,6 kg moist biomass was rinsed by distilled water and 0.5M $CH_3COOH$, then resespended in 2.5 L $H_2O$ and kept at 90° C. for 20–30 min. After that, it was diluted in 10 L $H_2O+70$ g $NaHCO_3$ (to achieve pH=6.0) and added 8 g of lyzosyme(Canadian Inovatech, Inc., Vancouver, Canada). Hydrolysis was done for 11.5 H in the shaking incubator at 54° C. Then, 3 g of trypsin was added for 6 hours.

110 ml $CH_3COOH$ was added to achieve pH=4.0 and was centrifuged on Beckman J-6 g at 4000 rpm for 30 min.

3. First Ultrafiltration.

Cartridge with the membrane capable of retaining compounds with molecular weight less than 3 000 D and with S=0.09 M.sup.2 at speed 2.5 L/h (Millipore Corp, USA) were used. 1.8 L solution with retained nuclear acids, phospholipids, and lysozyme was wasted. 10 L was passed through column with micro pore cationite in H-form in order to eliminate residual lysozyme and pigments.

4. Second Gel Chromatography

Sephadex G-25 and G-50 was used for separation of this novel glucosaminemuramyl pentapeptide. A distinct pick of neutral glucopeptide fraction was identified. This fraction of 1000 D molecular weight was collected and freeze dried. Amino acid analysis revealed L-Ala-, D-isoGly, D-Asp, and L-Lys in the ratio 2:1:1. The ratio of L-Ala and D-Ala was 1:1

EXAMPLE 2

Inhibition of TNF Alpha Cytotoxicity by GMHP

A549 cells (human lung cancer) were seeded in six-well plates, and after 24 h (70% confluence) treated with 25 ug/ml cycloheximide (CHX) and either 100 U/ml human TNF (Beoringer) or an agonist monoclonal antibody to FAS (Panerva) in concentration 200 ng/ml. GMDP, and GMHP were added just prior to the cytokine in the concentrations discussed in the figure legends. Twenty hours after the treatment 20 ul of the cultured supernatant was removed and tested for the LDH activity in 96 well plates in triplicate. Samples were assayed on an EL340 Microplate reader (Biotec Instruments, Inc) at 490-nm wavelength. FIG. 1 demonstrates the effect of GMDP and GMHP on LDH release. One can see enhanced potency of GMHP in comparison with GMDP. The level of the LDH activity was comparable to LDH background release by control intact cells.

EXAMPLE 3

Effect of D-amino Acid on the Inhibition of TNF Alpha Cytotoxicity

The purpose of this experiment was to show the synergistic effect of NAG and D-glutamine on LDH release. Technically the experiment was similar to example 1. Both ingredients were added in concentration 1 ug/ml. One can see, that L-glutamine does not protect cells from TNF alpha cytotoxicity (FIG. 2). Almost 50% inhibition of LDH activity was noticed for NAG+D-glutamine composition. This example explains why GMHP possesses more potency compared to GMDP. The glucosamine muramyl hexapeptide has 3 D-amino acids while GMDP has only one D-isoglutamine.

What is claimed is:

1. A method of preparation of therapeutically useful glucosamine-muramyl peptides comprising:
preparing a biomass containing non-pathogenic gram-positive bacteria to obtain bacterial peptidoglycans;
hydrolyzing the bacterial peptidoglycan with lysozymes and endopeptidases to produce a hydrolysate; and
filtering the hydrolysate with a membrane to obtain a filtrate containing compounds having molecular weights of 3000 D or less, wherein said compounds include therapeutically useful glucosamine-muramyl peptides.

2. The method of claim 1 wherein the membrane is adapted to separate compounds having molecular weights of less than 1,000 D.

3. The method of claim 1 further comprising the step of:
collecting said glucosamine-muramyl peptides by nanofiltration with reverse osmosis.

4. The method of claim 1 where said endopeptidase is capable of hydrolyzing cross-bridge peptide bonds.

5. The method of claim 1 where said endopeptidase is capable of hydrolyzing stem peptide bonds.

6. The method of claim 1 where said non-pathogenic gram-positive bacterium is selected from the group consisting of a Lactic Acid Bacterium, Lactobacillales, *Lactobacillus, Lactobacillus bulgaricus, Bifidobacterium* and *Streptococcus thermophilus*.

7. The method of claim 1 where said therapeutically useful glucosamine-muramyl peptide is selected from the group consisting of glucosamine-muramyl dipeptide, glucosamine-muramyl tripeptide, glucosamine-muramyl tetrapeptide, glucosamine-muramyl pentapeptide, glucosamine-muramyl hexapeptide, and glucosamine-muramyl octapeptide.

8. The method of claim 1 where said glucosamine-muramyl peptide is GMDP or GMDPA.

9. The method of claim 1 where said glucosamine-muramyl peptide contains two or more D-amino acids.

10. The method of claim 1 wherein said glucosamine-muramyl peptide has a formula of N-acetyl-glucosamine-N-acetyl-muramyl-L-Alanine-R1-R2-[R3]-D-Alanine where R1 is D-iso-Glutamine or D-Glutamic acid, R2 is L-Lysine or L-Ornithine, and R3 is an amino acid residue selected from the group Aspartic acid, Asparagine, Glutamic acid, Glutamine, iso-Glutamine, Glycine, Alanine, Serine, Threonine, Lysine, Ornithine.

11. The method of claim 10, wherein the peptide is selected from the group consisting of N-acetyl-glucosamine-N-acetyl-muramyl-L-Ala-D-isoGlu-L-Lys-D-Ala, N-acetyl-glucosamine-N-acetylmuramyl-L-Ala-D-isoGlu-L-Lys-(L-Gly)-D-Ala, N-Acetyl-N-glucosamine-N-Acetyl-muramyl-L-Ala-isoGlu-L-Lys, N-Acetyl-glucosamine-N-Acetylmuramyl-L-Ala-D-isoGlu-L-Lys-D-Asp-D-Ala (GMHP), N-Acetyl-N-glucosamine-N-Acetyl-muramyl-L-Ala-isoGlu-L-Lys-(D-Asp)-D-Ala, N-Acetyl-N-glucosamine-N-Acetyl-muramyl-L-Ala-isoGlu-L-Orn-(D-Ser-D-Asp)-D-Ala, N-Acetyl-N-glucosamine-N-Acetyl-muramyl-L-Ala-isoGlu-L-Orn-(D-Asp)-D-Ala, N-Acetyl-glucosamine-N-Acetyl-muramyl-L-Ala-isoGlu-L-Lys-(L-Ser)-D-Ala-L-Ala, N-Acetyl-glucosamimee-N-Acetylmuramyl-L-Ala-D-isoGlu-L-Lys-(L-Ser-L-Ala)-D-Ala-L-Ala, N-Acetyl-glucosamine-N-Acetylmuramyl-L-Ala-D-isoGlu-L-Lys-(L-Ser-L-Ala-L-Thr-L-Ala)-D-Ala, and N-Acetyl-glucosamine-N-Acetyl-muramyl-L-Ala-D-isoGlu-L-Lys-(D-Asp)-D-Ala.

12. The method of claim 1 wherein said glucosamine-muramyl peptide has a formula of N-acetyl-glucosamine-N-acetyl-muramyl-L-Ala-D-isoGlu-R1-(R3)-R2, N-acetyl-glucosamine-N-acetyl-muramyl-L-Ala-D-isoGLU-R1-(R3)-R2, or N-acetyl-glucosamine-N-acetyl-muramyl-L-Ala-D-isoGlu-R1-R2, wherein R1 is lysine or omithine, R2 is D-alanine, L-alanine, D-aspartic acid, L-glycine, L-serine, D-serine, or L-threonine, and R3 is L-glycine, D-asparagine, or D-glutamine.

13. The method of claim 1 where said glucosamine-muramyl peptide contains three D-amino acids.

14. The method of claim 1 where peptidoglycan of the said non-pathogenic gram-positive bacterium does not contain diaminopimelic acid.

15. The method of claim 1 where peptidoglycan of the said non-pathogenic gram-positive bacterium has lysine in the third position of the stem peptide.

16. The method of claim 1 where peptidoglycan of the said non-pathogenic gram-positive bacterium has omithine in the third position of the stem peptide.

* * * * *